United States Patent
Krammer

(10) Patent No.: US 9,392,997 B2
(45) Date of Patent: Jul. 19, 2016

(54) DEVICE AND METHOD FOR DETERMINING A FERTILE PHASE OF A WOMAN BY ASCERTAINING A $CO_2$ PARTIAL PRESSURE IN A RESPIRATORY GAS OF THE WOMAN

(75) Inventor: Gert Krammer, Graz (AT)

(73) Assignee: Carbomed Medical Solutions GmbH & Co KG, Gratwein (AT)

( * ) Notice: Subject to any disclaimer, the term of this patent is extended or adjusted under 35 U.S.C. 154(b) by 778 days.

(21) Appl. No.: 13/699,504

(22) PCT Filed: May 25, 2011

(86) PCT No.: PCT/EP2011/058589
§ 371 (c)(1),
(2), (4) Date: Feb. 4, 2013

(87) PCT Pub. No.: WO2011/147888
PCT Pub. Date: Dec. 1, 2011

(65) Prior Publication Data
US 2013/0178717 A1    Jul. 11, 2013

(30) Foreign Application Priority Data

May 25, 2010 (AT) .................................. A 847/2010

(51) Int. Cl.
*A61B 10/00* (2006.01)
*A61B 5/083* (2006.01)
(Continued)

(52) U.S. Cl.
CPC ............... *A61B 10/0012* (2013.01); *A61B 5/01* (2013.01); *A61B 5/082* (2013.01); *A61B 5/0836* (2013.01);
(Continued)

(58) Field of Classification Search
CPC ...... A61B 5/082; A61B 5/0836; A61B 5/097; A61B 10/0012; A61B 2010/0087
See application file for complete search history.

(56) References Cited

U.S. PATENT DOCUMENTS

| 4,346,584 | A | | 8/1982 | Boehringer |
| 6,102,868 | A | * | 8/2000 | Banner et al. ................. 600/484 |

(Continued)

FOREIGN PATENT DOCUMENTS

| CA | 2288281 | * | 11/1998 |
| DE | 28 13 518 | | 7/1979 |

(Continued)

OTHER PUBLICATIONS

Machine translation of DE 102009038238.*

(Continued)

*Primary Examiner* — Devin Henson
(74) *Attorney, Agent, or Firm* — Greenblum & Bernstein, P.L.C.

(57) ABSTRACT

The invention relates to a device (1) for determining a fertile phase of a woman by ascertaining a $CO_2$ partial pressure in a respiratory gas of the woman in several consecutive breaths, comprising an inlet for receiving the respiratory gas, and an outlet, a sample chamber (2), into which the respiratory gas can be conducted, a measuring module (3) with a measuring element (4) with which a $CO_2$ concentration in the respiratory gas in the sample chamber (2) can be measured, optionally a pressure sensor (5) for measuring an air pressure, a processor (7) for processing measured data obtained by means of the measuring module (3) and the pressure sensor (5), and at least one output unit (9) for outputting a result of the measured data. So that the method can be carried out by a woman herself quickly and nevertheless with high precision, it is provided according to the invention that the device (1) is embodied as a hand-held device and an algorithm is stored in the processor (7), with which with a measurement based on several immediately consecutive breaths a predetermined reproducibility criterion regarding an end expiratory $CO_2$ partial pressure of the respiratory gas can be tested, wherein, if the reproducibility criterion is met, the at least one output unit (9) outputs and/or signals and/or displays whether a fertile phase applies. Furthermore, the invention relates to a method for determining a fertile phase of a woman by ascertaining an end expiratory $CO_2$ partial pressure in a respiratory gas and comparison of the measured data thus obtained with measured data in the follicle phase outside the fertile phase.

30 Claims, 1 Drawing Sheet

Figure 1:
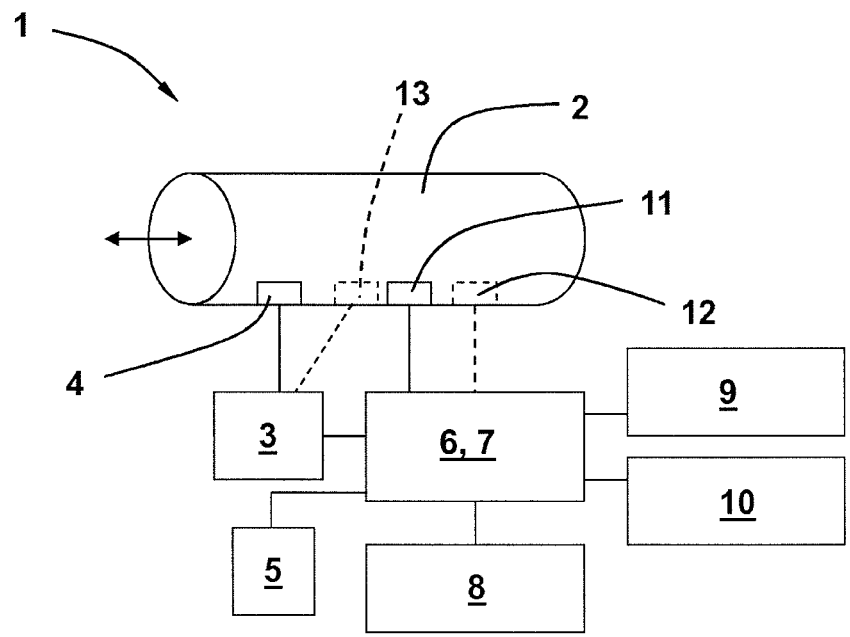

(51) Int. Cl.
*A61B 5/09* (2006.01)
*A61B 5/01* (2006.01)
*A61B 5/08* (2006.01)
*A61B 5/097* (2006.01)
*A61B 5/00* (2006.01)

(52) U.S. Cl.
CPC . *A61B 5/09* (2013.01); *A61B 5/097* (2013.01); *A61B 5/7278* (2013.01); *A61B 5/742* (2013.01); *A61B 5/7405* (2013.01); *A61B 2010/0087* (2013.01)

(56) References Cited

U.S. PATENT DOCUMENTS

| | | | |
|---|---|---|---|
| 8,211,035 B2* | 7/2012 | Melker et al. | 600/532 |
| 2002/0138213 A1* | 9/2002 | Mault | 702/32 |
| 2003/0004403 A1* | 1/2003 | Drinan | A61B 5/14539 600/301 |
| 2008/0119752 A1 | 5/2008 | Flanagan | |
| 2011/0046497 A1* | 2/2011 | Abraham-Fuchs et al. | 600/532 |

FOREIGN PATENT DOCUMENTS

| | | | |
|---|---|---|---|
| DE | 297 07 771 | | 8/1998 |
| DE | 102009038238 | * | 8/2009 |
| WO | WO 98/49536 | | 11/1998 |
| WO | WO 00/28881 | | 5/2000 |

OTHER PUBLICATIONS

Espacenet Biliographic data for DE 102009038238.*
K.-T. Moeller et al., "J. Fertil. Reprod.", 2003, pp. 7-12.
Dutton et al., "CO2 Sensitivity changes during the menstrual cycle." J. App. Physiol. Aug. 1989; 67(2); 517-22.
Hadziomerovic et al., "The biphastic pattern of end-expiratory carbon dioxide pressure: a method for identification of the fertile phase of the menstrual cycle." Fertil. Steril. Sep. 2008; 90(3): 731-6. Epub, Oct. 23, 2007.
Austrian Office Action and Search Report dated Dec. 3, 2010 in related Austrian Application No. A847/2010, along with partial English-language translation thereof.
European Office Action dated Oct. 17, 2013 in related European Application No. 11723915.2.

* cited by examiner

DEVICE AND METHOD FOR DETERMINING A FERTILE PHASE OF A WOMAN BY ASCERTAINING A $CO_2$ PARTIAL PRESSURE IN A RESPIRATORY GAS OF THE WOMAN

The invention relates to a device for determining a fertile phase of a woman by ascertaining a $CO_2$ partial pressure in a respiratory gas of the woman in several consecutive breaths, comprising an inlet for receiving the respiratory gas, and an outlet, a sample chamber, into which the respiratory gas can be conducted, a measuring module with a measuring element with which a $CO_2$ concentration in the respiratory gas in the sample chamber can be measured, optionally a pressure sensor for measuring an air pressure, a processor for processing measured data obtained by means of the measuring module and the pressure sensor, and at least one output unit for outputting a result of the measured data.

Furthermore, the invention relates to a method for determining a fertile phase of a woman by ascertaining an end expiratory $CO_2$ partial pressure in a respiratory gas of the woman and comparison of the measured data thus obtained with measured data in the follicle phase outside the fertile phase.

It is known from the prior art that a composition of a respiratory gas of a woman changes during the menstrual cycle. It was already possible to show in around 1940 that an end expiratory $CO_2$ partial pressure in the luteal phase is clearly below that in the follicle phase. In a detailed study it was established that by a measurement of the end expiratory $CO_2$ partial pressure a reliable cycle monitoring can be ensured, since the end expiratory $CO_2$ partial pressure already starts preovulation at the beginning of the fertile phase (K.-T. Moeller et al., J. Fertil. Reprod. 2003, 7). The measuring apparatus used in this study is very complex, however, and hardly permits a quick measurement by untrained personnel, in particular a woman herself.

WO 98/49536 A2 discloses a device for determining a woman's time of ovulation, in which likewise a measurement of the $CO_2$ partial pressure in the respiratory gas of a woman is used for a statement about the fertile phase. The device can be embodied in a small and transportable manner and makes it possible for it to be carried with her by a user.

Within the scope of the present invention it was recognized that a physical calmness of the woman or test subject can be decisive for a reliable measurement of the end expiratory $CO_2$ partial pressure. A physical calmness is expressed, as has been recognized, in measured data constant at least within certain tolerance ranges with immediately consecutive breaths. If there is physical calmness and if the measured data are constant within the predetermined tolerance ranges, however, a measurement can be completed quickly and accurately.

On the basis of this finding, the object of the invention is to disclose a device of the type mentioned at the outset, with which a determination of the fertile phase can be carried out quickly and nevertheless accurately even by untrained personnel or the woman herself.

A further object of the invention is to disclose a method of the type referenced at the outset, with which a fertile phase can be determined quickly and reliably by a woman or optionally a third party without expert assistance, in particular by the woman herself.

The object is attained according to the invention in that with a device of the type mentioned at the outset the device is embodied as a hand-held device and an algorithm is stored in the processor, with which with a measurement based on several immediately consecutive breaths a predetermined reproducibility criterion regarding an end expiratory $CO_2$ partial pressure of the respiratory gas can be tested, wherein, if the reproducibility criterion is met, the at least one output unit outputs and/or signals and/or displays whether a fertile phase applies.

One advantage achieved with a device according to the invention is to be seen in particular in that with a small device that is hand-operated or that can be hand-operated a precise analysis can be carried out quickly whether a fertile phase of a woman applies. It is thereby furthermore advantageous that a measurement time is minimized based on the provided reproducibility criterion, because e.g. a signal is emitted as soon as the reproducibility criterion has been met. It is also ensured that false analyses due to physical stress are virtually ruled out, since the reproducibility criterion is not met until it has been met in several consecutive measurements. If a woman is out of breath, for example, due to physical stress, the measurement is continued until the referenced reproducibility criterion has been achieved. This makes it possible for the measurement to be carried out by untrained, inexpert personnel or the woman herself, wherein in this context the embodiment of the device as a hand-held device is additionally an advantage, because the hand-held device has a corresponding manageability and the woman can lie down, for example, during the measurement in order to establish a physical calmness necessary for the measurement.

Based on the reproducibility criterion, individual measurements of the end expiratory $CO_2$ partial pressure are tested with respect to one another and when a reproducibility is reached for a predetermined number of consecutive measurements, the measurement is completed. In this regard a tolerance window is defined in advance in which the individual measured data must lie in order to meet the reproducibility criterion.

It is preferably provided that the algorithm based on the measured data of a cycle calculates a base line for the end expiratory $CO_2$ partial pressure in the follicle phase outside the fertile phase, so that consequently deviations from the base line and thus a fertile phase can be recognized reliably.

Furthermore, it can be preferably provided that the algorithm takes into consideration measured data of the end expiratory $CO_2$ partial pressure of several preceding cycles with an interpretation of the measured data.

If several measurements are carried out on one day, which in view of the approach of a fertile phase definitely can occur, the algorithm calculates a sliding daily average so that an averaging and thus a refinement of the measured data also takes place in this respect or a higher validity of the result of the same is given.

The output unit can carry out virtually any output when the reproducibility criterion has been reached. It is possible, for example, that a slip is output, on which the measured data together with result are noted. It is likewise possible that the measured data or a result of the measurement is displayed directly on the device by means of color coding or color code on a display of the device. Alternatively or simultaneously, it can also be advantageous since the device is hand-operated and during the measurement a view of the device can be obstructed, in particular when the woman herself measures and is thereby lying down, that an acoustic signal is emitted.

It is also particularly preferred that a temperature sensor is provided in the sample chamber. Alternatively, a temperature sensor and a moisture sensor can be provided in the sample chamber. A correction with respect to a water vapor partial pressure can thereby take place, which under certain circumstances can distort a result by up to 5%.

The measuring module and the associated measuring element can be embodied as desired per se. Preferably, the measuring module, however, comprises a measuring element that operates with IR radiation of one or more wavelengths. For example, an IR spectroscope can be provided. With an IR spectroscope a $CO_2$ concentration in a respiratory gas can be determined in a particularly simple manner. The IR spectroscope can optionally also be a photoacoustic IR spectroscope.

Alternatively, the measuring module can comprise an electrochemical sensor or an acoustic sensor for measuring the $CO_2$ concentration.

In particular for a measurement in a main flow method it is favorable if the measuring module comprises a solids sensor for measuring the $CO_2$ concentration on the basis of an ion conductivity. A method of this type meets the requirements for a quick measurement in the main flow method.

It is also possible for several sensors to be provided at the same time, wherein the results of all sensors can be taken into consideration.

With respect to measured data that are as accurate as possible and an avoidance of a condensate formation, it can also be preferred that a device for thermostatting the sample chamber is provided.

A measurement can be carried out in the main flow method or in the partial flow method. The main flow method is fundamentally preferred, since only a very low flow resistance is opposed to the respiratory gas. However, it is also possible to carry out a measurement only in the exhaled respiratory gas, wherein for this a pump is advantageously provided, with which a certain volume of the respiratory gas can be conducted out of a space lying between the inlet and the sample chamber into the sample chamber.

The device can furthermore comprise a mouthpiece. In principle it is possible for respiratory gas or a sample volume to be provided through a respiratory mask or possibly also a nasal tube for measurement in the sample chamber. However, a mouthpiece is the simplest alternative and has also proven to be very practicable with respect to precision.

In the sample chamber a further measuring element e.g. a heated resistance element or a propeller, can be provided with which a breathing rate can be measured. By means of a measurement of the breathing rate an additional variable can be taken into consideration in the reproducibility criterion.

The further object of the invention is achieved by a method of the type mentioned at the outset when with a measurement in a sample chamber, in particular with a device according to the invention, based on several immediately consecutive breaths a reproducibility criterion predetermined with respect to the end expiratory $CO_2$ partial pressure of the respiratory gas is tested and at least one output unit outputs a signal when the reproducibility criterion for a predetermined number of breaths has been achieved and it is output and/or signaled and/or displayed by the output unit whether a fertile phase applies.

One advantage achieved with a method according to the invention is to be seen in that the method permits a quick and nevertheless precise and reliable analysis with respect to a possible fertile phase of a woman. The method can optionally also be carried out by the woman herself, wherein when the reproducibility criterion has been reached, the measurement is ended and a signal is output e.g. by the output unit, so that the woman passively recognizes the end of the measurement. In addition, the result of the measurement is output, signaled and/or indicated in another manner by means of the output unit. In this respect it is possible that firstly an end of the measurement e.g. is signaled acoustically and subsequently a measurement result is shown on a display. However, it can also be output immediately with the end of the measurement, for example by means of words (fertile or not fertile) via a small loudspeaker.

It is preferably provided that a base line for the $CO_2$ partial pressure in the follicle phase outside the fertile phase is calculated based on the measured data of a cycle so that consequently deviations from the base line and thus a fertile phase is reliably discernible.

It is particularly preferred that the measured data of several preceding cycles are taken into consideration in an interpretation of the measured data. A measuring accuracy and thus also a precision of the prediction of fertile days can thereby be increased.

In the case of a multiple measurement on one day, preferably a sliding daily average is calculated with respect to a high measuring precision.

An end of the measurement or an achievement of the reproducibility criterion can be carried out for example by display on a display of the device used or output of a measurement slip. However, it is preferably provided, in particular when the device used is a hand-held device, that when the reproducibility criterion is reached, an acoustic signal is output. The woman can then concentrate completely on calm breathing during the measurement without having to look at the device. This also results in the advantage that the device can be embodied to be particularly small, in particular with a size that corresponds approximately to the size of a hand. Alternatively, a color-coded image can also be carried out, when a view of a display of the device is not restricted.

The determination of the $CO_2$ partial pressure can be carried out in any desired manner. It is preferably provided that the determination of the $CO_2$ concentration is carried out by an IR measuring process, since reliable measuring results can be achieved through this method.

It is advantageously provided that a water vapor partial pressure is calculated from a temperature measurement in the sample chamber and/or a temperature measurement and a measurement of an air humidity in the sample chamber and is taken into consideration as a correction variable. Tests have shown that the measurement results can be improved in terms of accuracy by up to 5% if the measured data are corrected accordingly.

For the improvement of a validity of the measurement or minimization of a risk, a measured result can be combined with a measured result of a further method for determining a fertile phase of the woman, preferably a basal temperature determination.

It can be provided that the measured data of several preceding cycles are stored and can be retrieved so that a comparison with older measurement results is possible for a user.

In order to achieve a precise measurement result before a first measurement and/or between measurements, a calibration by means of known gas concentrations can be carried out.

In the sample chamber with a further measuring element, e.g. a heated resistance element or a propeller, a breathing rate can be measured and preferably taken into consideration as a variable in meeting the reproducibility criterion.

Figure 2:
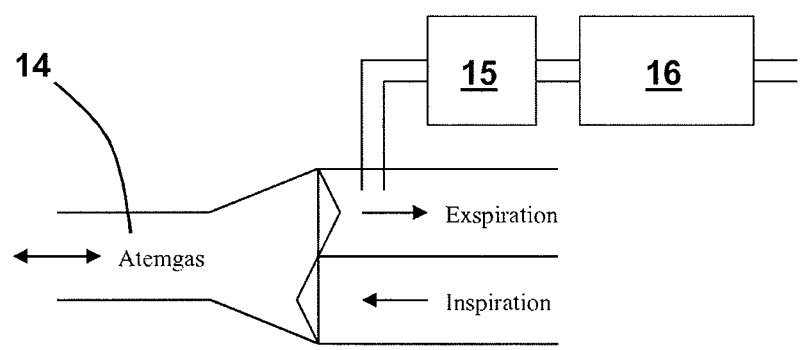

Further features, advantages and effects of the invention are shown by the exemplary embodiment shown below. In the drawing, to which reference is made, they show FIG. 1 a diagrammatic representation of a measurement setup, which can be used for a main flow or partial flow method;

FIG. 2 a diagrammatic representation of a partial flow method.

FIG. 1 shows diagrammatically a device 1 or a measurement setup. The device 1 is embodied as a hand-held device, in particular with a plastic housing, which can easily be held by a woman in one hand. Furthermore, the device 1, preferably embodied in an elongated manner has an end mouthpiece into which the woman can breathe.

The device 1 comprises a tubular sample chamber 2 with a measuring element 4 for determining a $CO_2$ concentration in a respiratory gas. Furthermore a measurement module 3 is provided, which can be used for operating the measuring element 4 and for amplifying a measurement signal and for these purposes is connected to the measuring element 4. The measuring element 4 preferably operates with IR radiation of one or several wavelengths, so that by means of measurement in the infrared range of the electromagnetic spectrum a $CO_2$ concentration in the sample chamber 2 can be determined from the respiratory gas located there. The measuring module 3 is connected to an analog-to-digital converter 6 or a processor unit 7. The processor unit 7 in turn is connected to a memory 8 and a pressure sensor 5 for detecting an air pressure; the pressure sensor 5 is not mandatory if the device 1 is calibrated with an external sensor before the first use. Furthermore an input unit 10 as well as an output unit 9 are provided. In addition, a temperature sensor 11 and advantageously a moisture sensor 12 are also located in the sample chamber 2. Through these additional sensors it is possible to correct measured data with respect to a water vapor partial pressure of the respiratory gas. Furthermore, a heated resistance element 13 for measuring a breathing rate in the sample chamber 2 can be provided, so that the breathing rate can be taken into consideration as a control variable for evaluating the measured data.

FIG. 2 shows a partial flow method in which the respiratory gas is deflected via a valve system. Advantageously, a predetermined constant volume of the exhaled gas is transported from an inlet region 14 with the aid of a pump 15 to a measuring setup 16 according to FIG. 1.

When carrying out a measurement, which can be carried out by a woman herself, the woman takes the device 1 and places the mouthpiece in order thereafter to breathe in and out at physical rest. An end expiratory $CO_2$ concentration is measured thereby with the measuring module 3. Thereafter the measured data are converted into a partial pressure by means of the likewise measured current air pressure and corrected by the water vapor partial pressure. The measured data recorded consecutively are stored and tested with respect to a reproducibility criterion. The reproducibility criterion is established in advance. For example, it can be provided that the reproducibility criterion is met when several, e.g. five, consecutive measurements lie within a predetermined signal window of for example 1 mm Hg of the $CO_2$ partial pressure. Naturally, the signal window in principle can be set as desired. Expediently, the signal window is selected such that on the one hand a sufficient accuracy of a measurement is ensured, on the other hand for this, however, a minimum of repetitions is sufficient. As soon as the reproducibility criterion has been met, the output device 9 of the device 1 emits a preferably acoustic signal and/or provides a color coded image optionally on a display of the device so that the user can end the measurement; at the same time a representation takes place of the measured result e.g. on a display of the device 1. This approach ensures that rapidly reliable measured data are obtained even if there are no trained staff present.

The invention claimed is:

1. A device for determining a fertile phase of a woman by ascertaining a $CO_2$ partial pressure in a respiratory gas of the woman in several consecutive breaths, comprising:

an inlet for receiving the respiratory gas,
an outlet, a sample chamber, into which the respiratory gas is conducted,
a measuring module with a measuring element with which a $CO_2$ concentration in the respiratory gas in the sample chamber is measurable,
a processor for processing measured data obtained by the measuring module, and
at least one output unit for outputting a result of the measured data,
wherein the device is embodied as a hand-held device and an algorithm is stored in the processor, with which with a measurement based on several immediately consecutive breaths a predetermined reproducibility criterion regarding an end expiratory $CO_2$ partial pressure of the respiratory gas is testable,
wherein, if the reproducibility criterion is met, the at least one output unit outputs and/or signals and/or displays whether a fertile phase applies,
wherein the predetermined reproducibility criterion is met when the measured data based on several immediately consecutive breaths are within a predetermined tolerance range; and
wherein the algorithm based on the measured data of a cycle calculates a base line for the end expiratory $CO_2$ partial pressure in a follicle phase outside the fertile phase.

2. The device according to claim 1, wherein the algorithm takes into consideration measured data of the end expiratory $CO_2$ partial pressure of several preceding cycles with an interpretation of the measured data.

3. The device according to claim 1, wherein if several measurements are carried out on one day, the algorithm calculates a sliding daily average.

4. The device according to claim 1, wherein when the reproducibility criterion is met, a color code and/or an acoustic signal is emitted with the output device.

5. The device according to claim 1, wherein a temperature sensor is provided in the sample chamber.

6. The device according to claim 5, further comprising a moisture sensor provided in the sample chamber.

7. The device according to claim 1, wherein the measuring module comprises a measuring element that operates with IR radiation of one or more wavelengths.

8. The device according to claim 1, wherein the measuring module comprises a photoacoustic IR spectroscope.

9. The device according to claim 1, wherein the measuring module comprises an electrochemical sensor for measuring the $CO_2$ concentration.

10. The device according to claim 1, wherein the measuring module comprises an acoustic sensor for measuring the $CO_2$ concentration.

11. The device according to claim 1, wherein the measuring module comprises a solids sensor for measuring the $CO_2$ concentration on the basis of an ion conductivity.

12. The device according to claim 1, wherein a device for thermostatting the sample chamber is provided.

13. The device according to claim 1, wherein a pump is provided, with which a certain volume of the respiratory gas is conducted out of a space lying between the inlet and the sample chamber into the sample chamber.

14. The device according to claim 1, wherein the device comprises a mouthpiece.

15. The device according to claim 1, wherein in the sample chamber a further measuring element is provided with which a breathing rate is measurable.

16. The device according to claim 15 wherein the measuring element comprises a heated resistance element or a propeller.

17. The device according to claim 1, further comprising a pressure sensor for measuring an air pressure, wherein the processor additionally processes measured data obtained by the pressure sensor.

18. A method for determining a fertile phase of a woman by ascertaining an end expiratory $CO_2$ partial pressure in a respiratory gas of the woman and comparison of measured data thus obtained with measured data in a follicle phase outside the fertile phase, wherein with a measurement in a sample chamber based on several immediately consecutive breaths a reproducibility criterion predetermined with respect to the end expiratory $CO_2$ partial pressure of the respiratory gas is tested and at least one output unit outputs a signal when the reproducibility criterion for a predetermined number of breaths has been achieved and it is output and/or signaled and/or displayed by the output unit whether a fertile phase applies,
    wherein the reproducibility criterion is met when the measured data based on the predetermined number of consecutive breaths are within a predetermined tolerance range; and
    wherein a base line for the end expiratory $CO_2$ partial pressure in the follicle phase outside the fertile phase is calculated based on the measured data of a cycle.

19. The method according to claim 18, wherein the measured data of several preceding cycles are taken into consideration in an interpretation of the measured data.

20. The method according to claim 18, wherein if several measurements are carried out on one day, a sliding daily average is calculated.

21. The method according to claim 18, wherein when the reproducibility criterion has been met, an acoustic signal and/or a color coded image is outputted.

22. The method according to claim 18, further comprising ascertaining a $CO_2$ concentration, wherein the ascertainment of the $CO_2$ concentration is carried out by an IR measuring method.

23. The method according to claim 18, wherein a water vapor partial pressure is calculated from a temperature measurement in the sample chamber and/or from a temperature measurement and a measurement of an air humidity in the sample chamber and is taken into consideration as a correction variable.

24. The method according to claim 23, wherein the method for determining the fertile phase of the woman comprises a basal temperature determination.

25. The method according to claim 18, wherein a measured result is combined with a measured result of a further method for determining a fertile phase of the woman.

26. The method according to claim 18, wherein the measured data of several preceding cycles are stored and is retrievable.

27. The method according to claim 18, wherein before a first measurement and/or between measurements, a calibration is carried out using known gas concentrations.

28. The method according to claim 18, wherein in the sample chamber with a further measuring element a breathing rate is measured and is taken into consideration as a variable in meeting the reproducibility criterion.

29. The method according to claim 28, wherein the further measuring element comprises a heated resistance element or a propeller.

30. The method according to claim 18, wherein the method is performed using the device according to claim 1.

* * * * *